United States Patent
Stamenkovic et al.

(10) Patent No.: US 7,871,738 B2
(45) Date of Patent: Jan. 18, 2011

(54) NANOSEGREGATED SURFACES AS CATALYSTS FOR FUEL CELLS

(75) Inventors: Vojislav Stamenkovic, Naperville, IL (US); Nenad M. Markovic, Hinsdale, IL (US)

(73) Assignee: UChicago Argonne, LLC, Chicago, IL (US)

(*) Notice: Subject to any disclaimer, the term of this patent is extended or adjusted under 35 U.S.C. 154(b) by 0 days.

(21) Appl. No.: 12/338,736

(22) Filed: Dec. 18, 2008

(65) Prior Publication Data

US 2009/0247400 A1 Oct. 1, 2009

Related U.S. Application Data

(60) Provisional application No. 61/008,605, filed on Dec. 20, 2007.

(51) Int. Cl.
*H01M 4/02* (2006.01)
*B01J 21/18* (2006.01)

(52) U.S. Cl. .................................... 429/524; 502/185

(58) Field of Classification Search ................. None
See application file for complete search history.

(56) References Cited

U.S. PATENT DOCUMENTS

2004/0072061 A1* 4/2004 Nakano et al. ............... 429/44
2006/0083970 A1* 4/2006 Shibutani et al. ............ 429/30

OTHER PUBLICATIONS

Campbell, C.T., "Bimetallic Surface Chemistry", *Ann. Rev. Phys. Chem.*, 1990, pp. 775-837, vol. 41, Annual Reviews, Inc.
Debe et al., "Structural Characteristics of a Uniquely Nanostructured Organic Thin Film", *J. Vac. Sci. Technol. B.*, May/Jun. 1995, pp. 1236-1241, vol. 13, No. 3, American Vacuum Society, USA.
Gasteiger et al., "Activity Benchmarks and Requirements for Pt, Pt-alloy, and non-Pt Oxygen Reduction Catalysts for PEMFCs", *Applied Catalysis B: Environmental*, 2005, pp. 9-35, vol. 56, Elsevier B.V.
Gauthier et al., "Influence of the Transition Metal and of Order on the composition Profile of $Pt_{80}M_{20}(111)$ (M=Ni, Co, Fe) alloy surfaces: LEED Study of $Pt_{80}Co_{20}(111)$", *Surf. Sci.*, 1992, pp. 1-11, vol. 276, Elsevier Science Publishers B.V.
Greeley et al., "Electrochemical Dissolution of Surface Alloys in Acids: Thermodynamic Trends from First-Principles Calculations", *Electrochimica Acta*, 2007, pp. 5829-5836, vol. 52, Elsevier Ltd.
Greeley et al., "Electronic Structure and Catalysis on Metal Surfaces", *Annu. Rev. Phys. Chem.*, 2002, pp. 319-348, vol. 53, Annual Reviews.
Greeley et al., "Near-Surface Alloys for Hydrogen Fuel Cell Applications", *Catalysis Today*, 2006, pp. 52-58, vol. 111, Elsevier B.V.
Hammer et al., "Theoretical Surface Science and Catalysis—Calculations and Concepts", *Advances in Catalysis*, 2000, pp. 71-129, vol. 45, Academic Press.

Paulus et al., "Oxygen Reduction on Carbon-Supported Pt-Ni and Pt-Co Alloy Catalysts", *J. Phys. Chem. B*, 2002, pp. 4181-4191, vol. 106, American Chemical Society, USA.
Paulus et al., "Oxygen Reduction on High Surface Area Pt-Based Alloy Catalysts in Comparison to Well Defined Smooth Bulk Alloy Electrodes", *Electrochimica Acta*, 2002, pp. 3787-3798, vol. 47, Elsevier Science Ltd.
Peng, X., "Mechanisms for the Shape-Control and Shape-Evolution of Colloidal Semiconductor Nanocrystals", *Adv. Mater.*, Mar. 4, 2003, pp. 459-463, vol. 15, No. 4, Wiley-VCH Verlag GmbH & Co. KGaA, Weinheim.
Stamenkovic et al., "Changing the Activity of Electrocatalysts for Oxygen Reduction by Tuning the Surface Electronic Structure", *Angew. Chem. Int. Ed.*, 2006, pp. 2897-2901, vol. 45, Wiley-VCH Verlag GmbH & Co. KGaA, Weinheim.
Stamenkovic et al., "Effect of Surface Composition on Electronic Structure, Stability, and Electrocatalytic Properties of Pt-Transition Metal Alloys: Pt-Skin versus Pt-Skeleton Surfaces", *J. Am. Chem. Soc.*, 2006, pp. 8813-8819, vol. 128, American Chemical Society, USA.
Stamenkovic at al., "Improved Oxygen Reduction Activity on $Pt_3Ni(111)$ via Increased Surface Site Availability", *Science*, Jan. 26, 2007, pp. 493-497, vol. 315, www.sciencemag.org.
Stamenkovic et al., "Surface Composition Effects in Electrocatalysis: Kinetics of Oxygen Reduction on Well-Defined $Pt_3Ni$ and $Pt_3Co$ Alloy Surfaces", *J. Phys. Chem. B.*, 2002, pp. 11970-11979, vol. 106, American Chemical Society, USA.
Stamenkovic et al., "Trends in Electrocatalysis on Extended and Nanoscale Pt-bimetallic Alloy Surfaces", *Nature Materials*, Mar. 2007, pp. 241-247, vol. 6, Nature Publishing Group.
Sun et al., "Monodisperse FePt Nanoparticles and Ferromagnetic FePt Nanocrystal Superlattices", *Science*, Mar. 17, 2000, pp. 1989-1992, vol. 287, www.sciencemag.org.
Wang et al., "A General Approach to the Size- and Shape-Controlled Synthesis of Platinum Nanoparticles and Their Catalytic Reduction of Oxygen", *Angew. Chem. Int. Ed.*, 2008, pp. 3588-3591, vol. 47, Wiley-VCH Verlag GmbH & Co. KGaA, Weinheim.

* cited by examiner

*Primary Examiner*—Melvin C Mayes
*Assistant Examiner*—Sheng H Davis
(74) *Attorney, Agent, or Firm*—Foley & Lardner LLP

(57) ABSTRACT

A method of preparing a nanosegregated Pt alloy having enhanced catalytic properties. The method includes providing a sample of Pt and one or more of a transition metal in a substantially inert environment, and annealing the sample in such an environment for a period of time and at a temperature profile to form a nanosegregated Pt alloy having a Pt-skin on a surface. The resulting alloy is characterized by a plurality of compositionally oscillatory atomic layers resulting in an advantageous electronic structure with enhanced catalytic properties.

15 Claims, 5 Drawing Sheets

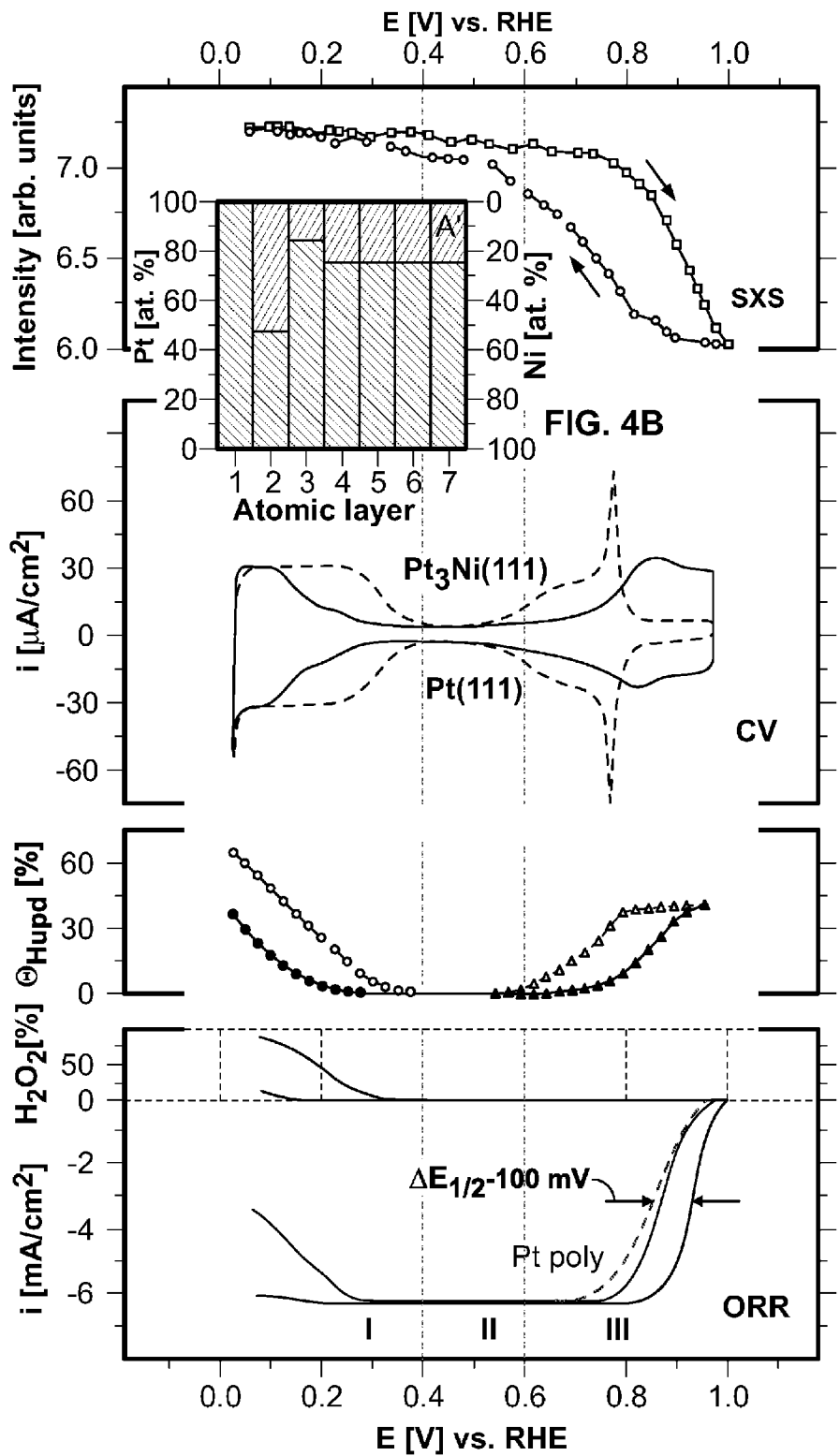

NANOSEGREGATED SURFACES AS CATALYSTS FOR FUEL CELLS

CROSS REFERENCE TO RELATED PATENT APPLICATIONS

The present application claims priority to U.S. Provisional Patent Application No. 61/008,605, filed Dec. 20, 2007 incorporated herein by reference in its entirety.

STATEMENT OF GOVERNMENT INTEREST

The United States Government claims certain rights in this invention pursuant to Contract No. W-31-109-ENG-38 between the United States: Government and the University of Chicago and/or pursuant to BE-AC02-06CH11357 between the United States Government and UChicago Argonne, LLC representing Argonne National Laboratory.

FIELD OF THE INVENTION

The present invention relates generally towards a new class of Platinum (Pt) multi-metallic catalysts. More particularly, the invention is directed to a catalyst having surface layers of a Pt based catalyst modified by annealing, which induces unique near-surface formations termed as nanosegregated surfaces. This catalyst is particularly advantageous for use in conjunction with fuel cells, such as polymer electrolyte feel cells.

BACKGROUND OF THE INVENTION

This section is intended to provide a background or context to the invention that is, inter alia, recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Fuel cells are rapidly becoming an important component in the energy industry; but currently costly Pt catalyst is typically a required component of the fuel cell. To make fuel cells commercial competitive at reasonable cost, the amount of Pt used in the fuel cell should be reduced by a factor of 4 to 5. Further, catalyst stability should be improved for longer term operation of the fuel cell. Pt based alloys embedded in high surface area carbon substrates have been developed that improve catalyst performance by a factor of two. However, these efforts have not increased catalyst stability, and have not reduced the total loading of Pt in the fuel cell stacks to acceptable levels. Additionally, the substantial overpotential for oxygen reduction reaction ("ORR") at practical operating current densities still causes a reduction of thermal efficiency. These efforts have resulted in systems that are well below thermodynamic limits (typically to about 43% at 0.7 V versus the theoretical thermal efficiency of 83% at the reversible potential for the ORR). Also, the dissolution and/or loss of the Pt surface area in the fuel cell cathode should be reduced for practical application of fuel cells.

SUMMARY OF THE INVENTION

New catalysts have been prepared based on the modification of Pt based alloys that can be in the form of bulk, thin films over various substrates, and/or nanoparticles materials, Nanosegregated surface layers of Pt alloyed with transition metals, such as Co, Ni, Fe, Ti, Cr, V, Zr and Mn, for example, have been constructed with selected compositions to establish advantageous electronic structures which greatly enhance the catalytic properties, particularly as used for fuel cells. The composition of the nanosegregated surfaces is highly oscillatory in the first few atomic layers for all crystallographic orientations including polycrystalline materials. However, nanosegregated surface structures with a {111} crystallographic orientation have yielded catalytic enhancement by a factor of about ninety, versus conventional Pt-carbon catalysts and about ten times that of a corresponding pure Pt {111} surface for a cathodic fuel cell reaction. The prepared catalysts are thus particularly useful in polymer electrolyte membrane fuel cells for applications such as in the automotive industry, by overcoming kinetic limitations for the oxygen reduction reaction ("ORR"). The prepared materials may also have application in energy storage devices, including batteries, and magnetic storage devices due to unique surface properties.

In one set of embodiments, a method of preparing a nanosegregated Pt alloy having enhanced catalytic properties, comprises providing a sample comprising an alloy of Pt and one or more of a transition metal. The sample is subsequently annealed in an substantially inert and/or reductive environment for a period and at a temperature profile to form a nanosegregated Pt alloy having a Pt-skin on a surface of the sample.

In another set of embodiments, a nanosegregated Pt alloy having enhanced catalytic properties, comprises an alloy of Pt with one or more of a transition metal, the alloy includes one or more layers proximate to a surface of the alloy. Each of the one or more layers have a concentration of Pt varying from the bulk concentration of Pt in the alloy and wherein the surface layer of the alloy comprises a Pt-skin.

Advantages and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 4A shows in situ characterization of $Pt_3Ni$ {111} surface in $HClO_4$ (0.1M) at 333K for surface X-ray scattering; and FIG. 4B shows the concentration profile from the data of FIG. 4A in atomic percent as a function of atomic layer;

FIG. 5 show cyclic voltammetry output in a designated potential area (solid line) compared to voltammetry output obtained from a Pt{111} surface (dashed line);

FIG. 6 shows surface coverage calculated from cyclic voltammetry polarization plots for Pt$_3$Ni{111} (solid curve) and Pt{111} (dashed curve) obtained from rotating ring disk electrode (RRDE) measurements with $\theta_{oxide}$ surface coverage by absorbed spectator oxygenated species;

FIG. 7 shows hydrogen peroxide production in a designated potential region;

FIG. 8 shows ORR currents measured on Pt$_3$Ni{111} (solid curve), Pt (dotted curve) and polycrystalline Pt (dashed curve)

DETAILED DESCRIPTION OF PREFERRED EMBODIMENTS

Figure 1A:
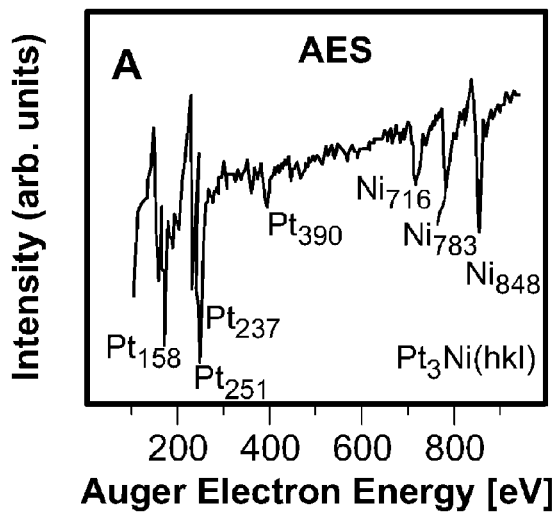
FIG. 1A shows Auger spectroscopy of a surface of a $Pt_3Ni$ single crystal in ultra high vacuum.
Figure 1B:
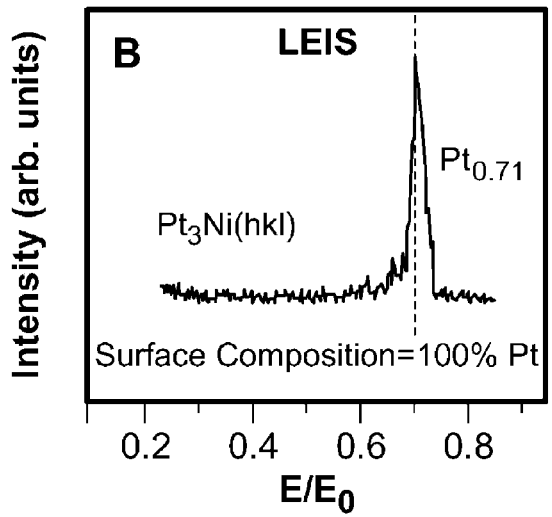
FIG. 1B shows low-energy ion scattering spectra in terms of $E/E_0$ for the $Pt_3Ni$ crystal where E is energy of the scattered electrons and $E_0$ in the incident ion beam energy.
Figure 1C:
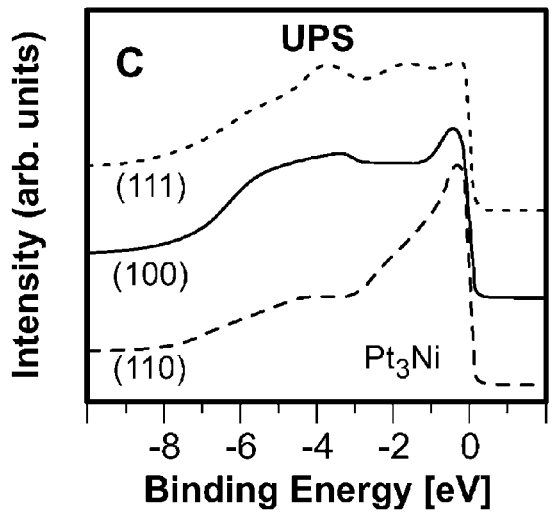
FIG. 1C show ultra-violet photoemission spectroscopy spectra of the $Pt_3Ni$ crystal.

To overcome the deficiencies of the conventional catalysts and attain advantageous commercial catalysts, various Pt based surface layers have been modified to achieve the desired catalytic activity, such as for use in polymer electrolyte membrane fuel cells. Cathode materials with well-characterized surfaces have been modified so that the mechanism of action can be attributed to a specific property at the atomic and molecular level of the surface. The materials are assessed to determine (i) whether the kinetics of the ORR are structure-sensitive, (ii) the composition of the topmost surface atomic layers (the segregation profile), and (iii) how alloying, usually described in the art in terms of the ligand effect or/and ensemble effect, alters the chemical properties of the surfaces. Aqueous electrochemical interfaces are complex in that they necessarily contain, solvent and electronic/ionic charge, and experimentally it can be challenging to use in situ surface-sensitive methods to characterize potential-induced changes in the surface properties and reactivity.

Pt alloyed with transition metals, such as Co, Ni, Fe, Ti, Cr, V, Zr and Mn, for example, have been constructed with selected compositions to establish advantageous electronic structures which greatly enhance the catalytic properties. The resulting nanosegregated Pt based alloys are prepared through an annealing of the alloy in a substantially inert and/or reductive environment. For example, the environment may be substantially N$_2$, H$_2$, or At gas, or mixtures thereof. Alternatively, annealing may be conducted under vacuum conditions. The annealing may be carried out for an appropriate time and an appropriate temperature profile for the alloy. In an embodiment, for example, an alloy of PtNi in the form of bulk, thin film and/or nanoparticles, is annealed for a period ranging from about 20 minutes to about 240 minutes at a substantially controlled temperature of between about 350° C. and 1000° C., In still other embodiments a non-constant annealing temperature profile may be used to obtain the nanosegregated Pt based alloy.

A combination of ex situ and in situ, for example, surface-sensitive probes and density functional theory (DFT) calculations is used to assess the ORR on Pt$_3$Ni(hkl) single-crystal surfaces. The surface properties that govern the variations in reactivity of Pt$_3$Ni catalysts are identified. The influence of surface structures, surface segregation, and inter-metallic bonding on ORR kinetics is determined. The results described herein are applicable to any Pt-transition multi-metallic alloy regardless of the crystalline nature of the material, i.e. nanosegregated surfaces with the Pt-skin topmost layer have been successfully generated on polycrystalline as well as on single crystalline catalysts.

Well-characterized PtNi single-crystal electrode surfaces were formed and characterized with UHV methods for surface preparation and surface analysis. These surfaces were transferred into the electrochemical environment without airborne contamination, and the stability of the UHV-prepared surface was determined with a combination of in situ surface-sensitive probes with electrochemical methods to obtain activity relationships in real time.

The results of the preparation and characterization of Pt$_3$Ni (hkl) alloy surfaces in UHV are summarized in FIGS. 1A-3C. The various surface-sensitive techniques that were used included low-energy electron diffraction (LEED), Auger electron spectroscopy (ABS), low-energy ion scattering (LEIS), and synchrotron-based high-resolution ultraviolet photoemission spectroscopy (UPS). Each of these methods has certain advantages, and each yield complementary information. The surface symmetry obtained from LEED analysis shows that, whereas the Pt$_3$Ni{111} surface exhibits a (1×1) pattern (FIG. 1D) (i.e, that of the bulk termination), the atomically less dense Pt$_3$Ni{100} surface shows a (1×5) reconstruction pattern (the so-called "hex" phase) in both the {011} and {01-1} directions (FIG. 1E). Analysis of the Pt$_3$Ni{110} LEED data (FIG. 1F) indicates that this surface may exhibit a mixture of (1×1) and (1×2) periodicities, the latter being known as the (1×2) missing-row structure (22).

The composition of the outermost atomic layer was obtained with LEIS, and after a final anneal, the surface atomic layer of all three Pt$_3$Ni(hkl) crystals were pure Pt (see FIG. 1B), the so-called Pt-skin structures. Evaluation has determined that segregation-driven near-surface compositional changes induced by annealing result in distinctive electronic properties of PtNi(hkl) alloys, and unique segregation profiles.

The surface electronic structures were obtained from the background-corrected UPS spectra. As summarized in FIG. 1C, the d-band density of states (DOS) is structure-sensitive, and the position of the (d-band center shifts from −2.70 eV$_{on}$ Pt$_3$Ni{110} to −3.10 eV$_{on}$ Pt$_3$Ni{111} to −3.14 eV on Pt$_3$Ni{100}. Furthermore, the DOS of the alloy surfaces is quite different from that of corresponding pure Pt single crystals; that is, on the {110}, {100}, and {111} alloy surfaces, the d-band center is downshifted by about 0.16, 0.24, and 0.34 eV, respectively. Chemisorption energies were evaluated to determine correlation with the average energy of the d-state on the surface atoms to which the adsorbate binds (i.e., the ligand effect). Results on the {111} surfaces were compared with the same composition and arrangement of surface atoms but with a different d-band center position. In this manner the difference between the electronic surface structures of Pt{111} and Pt$_3$Ni{111} affected the adsorption of spectator species and the kinetics of the ORR.

The stability of the surface after transfer from UHV into the electrochemical environment was also determined. Surface X-ray scattering (SXS) was used to characterize both the potential range of stability as well as the near-surface composition of the alloy in situ. Only results for Pt$_3$Ni{111} are necessary because they provide the most useful information about the annealing-induced changes in the surface structure and segregation profile. The Pt$_3$Ni{111} has the face-centered cubic (fcc) lattice with random occupation of sites by Pt and Ni; and this lattice gives rise to SXS indicia similar to that obtained from a monocrystalline fcc lattice. Sensitivity to atomic layer composition is enhanced by the use of anomalous x-ray scattering techniques in which the incident X-ray energy is tuned to an atomic adsorption edge of the material. Thus, from SXS, information is obtained about the structure and compositions, both in the surface and subsurface layers.

Figure 2A:
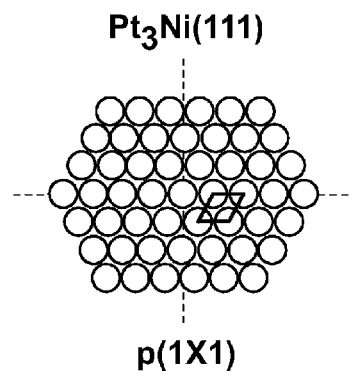
FIG. 2A shows a low-energy electron diffraction (LEED) pattern for $Pt_3Ni\{111\}$ and a corresponding model in FIG. 2B.
Figure 2D:
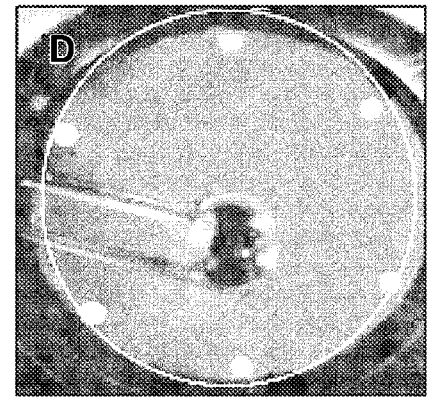
FIG. 2C shows a LEED pattern for $Pt_3Ni\{111\}$ and a corresponding model in FIG. 2D.
FIG. 2E shows another LEED pattern for $Pt_3Ni\{110\}$ and a corresponding model in FIG. 2F.
Figure 2B:
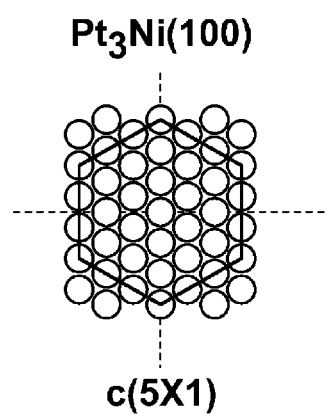
Figure 2E:
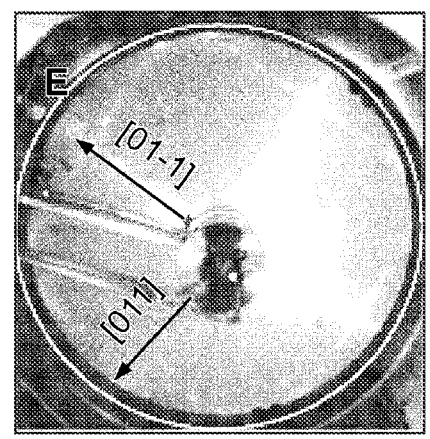

The termination of the $Pt_3Ni\{111\}$ lattice at the surface in terms of elemental composition and surface relaxation was determined by measurement and analysis of the crystal truncation rods (CTRs). The CTR analysis shows that, at 0.05 V, the first layer is composed entirely of Pt and, whereas the second atomic layer has an elevated level of Ni (about 52% of Ni as compared to 25% of Ni in the bulk), the third layer has an elevated level of Pt (about 87%) (FIG. 2A). Having determined the near-surface structure at 0.05 V, the potential was cycled while the scattered X-ray intensity was measured at a CTR position that is sensitive to surface relaxation and surface roughness (see FIG. 4A).

Both the $Pt_3Ni\{111\}$ surface structure as well as the segregation profile are completely stable over this potential range because the changes in the X-ray scattering signal are fully reversible, and the decrease in intensity at positive potential is consistent with an inward relaxation (contraction) of the surface atomic layer (this result is confirmed by similar measurements at other reciprocal lattice positions). The contraction of Pt surface atoms is induced by the adsorption of oxygenated species, which is determined by the Ni-induced modification of the Pt-skin electronic structure. A direct consequence of contraction of the topmost layer of Pt-skin at the potentials higher than 0.8 V is the increased stability of this surface over corresponding pure $Pt\{111\}$, which was additionally confirmed by prolonged cycling In the designated potential range. It is important to point out, that pure Pt catalysts exhibit expansion of the topmost layer at the potential higher than 0.8 V, which is considered to be precursor of Pt dissolution and one of the major limitations in fuel cell technology. This fundamental property of pure Pt catalysts has been completely modified in case of Pt-skin surfaces.

Figure 2C:
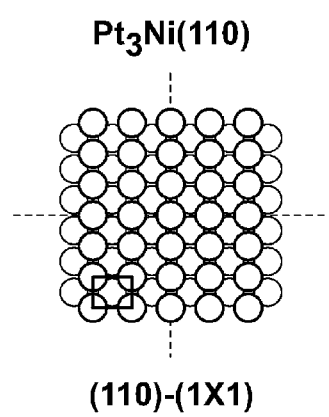
Figure 2F:
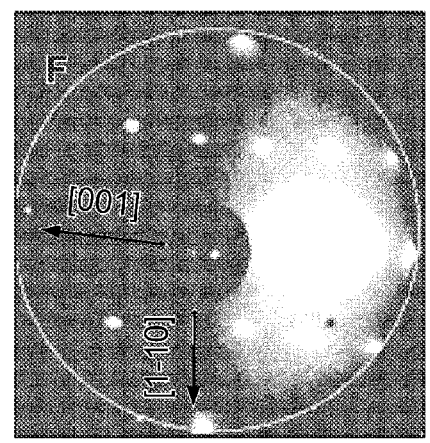
Figure 3A:
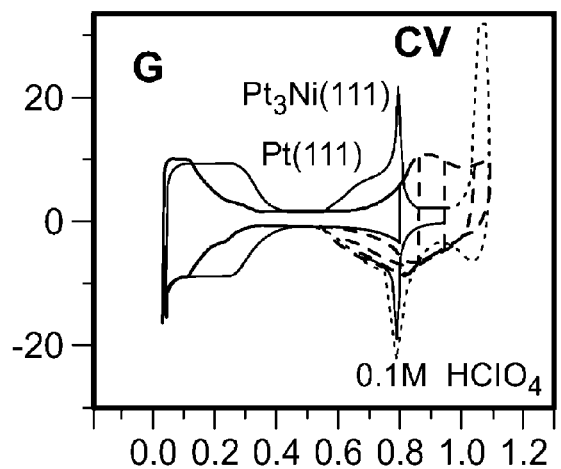
FIG. 3A shows cyclic voltammetry for the specimen in $HClO_4$ (0.1M) compared to the voltammetry output for the corresponding $Pt_3Ni\{111\}$ single crystal and $Pt\{111\}$.
Figure 3B:
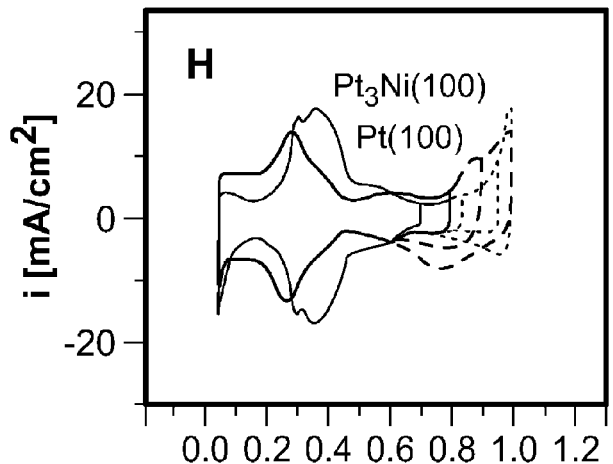
FIG. 3B shows similar plots as for FIG. 3A but for {100} crystallographic orientation of the surface.
Figure 3C:
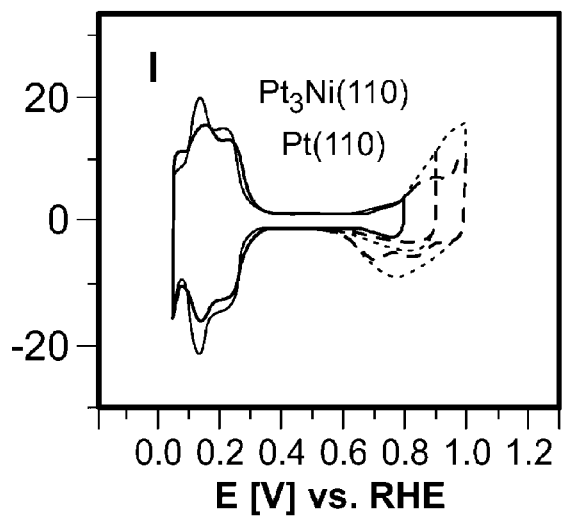
FIG. 3C shows cyclic voltammetry output for the reversible hydrogen electrode of the fuel cell and for both $Pt_3Ni\{110\}$ and $Pt\{110\}$.

The relationship between the surface electronic properties and the potential-dependent surface coverage by adsorbing species (the adsorption isotherms in FIG. 6) were established by comparing the experimentally determined position of the d-band centers to the fractional coverage of adsorbed hydrogen ($H^+ + e^- = H_{upd}$, where $H_{upd}$ refers to the underpotentially deposited hydrogen) between 0.05<E<0.4 V, where E is the applied potential, and the hydroxyl species ($2H_2O = OH_{ad} + H_3O^+ + e^-$, where $OH_{ad}$ is the adsorbed hydroxyl molecule) above 0.6 V (FIG. 2C). Inspection of the voltammograms in FIG. 5 revealed that on $Pt\{111\}$-skin, which consists of the same surface density of Pt atoms as $Pt\{111\}$, a negative shift of about 0.15 V in $H_{upd}$ formation and positive shift of about 0.1 V in $OH_{ad}$ formation occurred relative to $Pt\{111\}$. In agreement with the onset of adsorption, on $Pt_3Ni\{111\}$, the fractional coverage by $H_{upd}$ and $OH_{ad}$ ($\Theta_{Hupd}$ and $\Theta_{OHad}$) were dramatically reduced by 50 percent relative to $Pt\{111\}$, which is in agreement with the large downshift (0.34 eV) of the d-band center position on the Pt-skin structure. As shown In FIGS. 5 and 6, similar changes occurred for the other two single-crystal surfaces. On the $Pt\{100\}$-skin, $\Theta_{Hupd}$ was reduced by about 15 percent relative to $Pt\{100\}$, and $\Theta_{OHad}$ was reduced by about 25 percent. On $Pt_3Ni\{100\}$, small but clearly discernable decreases in $\Theta_{Hupd}$ of about 10% and the fractional coverage by $OH_{ad}$ ($\Theta_{OHad}$) of about 20 percent were observed relative to $Pt\{110\}$.

To quantitatively describe these effects, DFT calculations were performed using pseudopotentials and a plane-wave basis set on the adsorption of OH and $H_2O$ at 0.25 monolayer coverage on modeled $Pt\{111\}$ surfaces, with second atomic layers containing 0 or 50 percent Ni atoms. In acid solutions, $OH_{ad}$ would react with $H^+$ and form $H_2O$ on the catalyst surface. The change in the reversible potential $\Delta U°$ of the above reaction on $Pt\{111\}$ resulting from sublayer Ni atoms is $$\Delta U° = [E_{ads}(OH)_{Pt} - E_{ads}(OH)_{PtNi} - E_{ads}(OH)_{Pt} + E_{ads}(H_2O)_{PtNi}]/F \quad (1)$$

Here, $E_{ads}(OH)_{Pt}$, $E_{ads}(H_2O)_{Pt}$, $E_{ads}(OH)_{PtNi}$, and $E_{ads}(H_2O)_{PtNi}$ are the adsorption energies of OH and $H_2O$ on $Pt\{111\}$ with or without sublayer Ni atoms, respectively, and F is the Faraday constant. The DFT calculations show a positive shift of $\Delta U° = 0.10$ V when the sublayer has 50% Ni atoms. The experiment and theory substantially correspond and demonstrate an electronic effect of subsurface Ni on the Pt—OH chemical bonding.

The ORR is a multielectron reaction ($\frac{1}{2}O_2 + 2H^+ + 2e^- = H_2O$) that may include a number of elementary steps involving different reaction intermediates. The rate of the ORR can be expressed as:

$$i = nFKc_{O2}(1 - \Theta_{ad})^x \exp(-\beta FE/RT) \exp(-\Delta G_{ad}/RT) \quad (2)$$

where i is the measured current; n, F, K, E, x, β, γ, and R are constants; $c_{O2}$ is the concentration of $O_2$ in the solution, $\Theta_{ad}$ is the total surface coverage by adsorbed spectator species [hydroxyl and anions; for example, $OH_{ad}$ ($\Theta_{OH}$) and specifically adsorbed anions ($\Theta_{Aad}$)]; $\Delta G_{ad}$ is the Gibbs energy of adsorption of reactive intermediates, and T is temperature. In the derivation of Equation 2, it is assumed that (i) the ORR takes place on electrodes that are modified by $OH_{ad}$, anions, etc., and (ii) the reactive intermediates ($O_2$ and $H_2O_2$) are adsorbed to low coverage (i.e., they are not a substantial part of $\Theta_{ad}$)

Based on these assumptions, the kinetics of $O_2$ reduction are determined by the number of free Pt sites available for the adsorption of $O_2$ (the $1 - \Theta_{ad}$ term in Equation 2) and by the $\Delta G_{ad}$ of $O_2$ and reaction intermediates (the $\Delta G_{ad}$ term in Equation 2) on metal surfaces precovered by $OH_{ad}$. This reaction pathway and rate expression is used to first to analyze the effects of electronic properties on the kinetics of the ORR on $Pt_3Ni\{111\}$ and $Pt\{111\}$ and then, by comparing activities on different $Pt_3Ni(hkl)$ surfaces, to establish structure sensitivity.

FIG. 7 shows a characteristic set of polarization curves (the relation of i versus E) for the ORR on Pt-poly, $Pt\{111\}$, and $Pt_3Ni\{111\}$ surfaces in $HClO_4$ (0.1 M) at 333 K. For all three surfaces, the polarization curves exhibit two distinguishable potential regions. By starting at 0.05 V and scanning the electrode potential positively, well-defined diffusion-limiting currents from 0.2 to 0.7 V are followed by a mixed kinetic-diffusion control region between 0.8<E<1.0 V. FIG. 7 also reveals that the ORR kinetic is accelerated on the $Pt\{111\}$-skin relative to $Pt\{111\}$, causing the positive shift of 100 mV in the half-wave potential. Given that $\Theta_{OHad}$ is attenuated on the Pt-skin surface, the key parameter that determines the unexpectedly high catalytic activity of $Pt_3Ni\{111\}$ is the low coverage by $OH_{ad}$ [i.e., the $(1 - \Theta_{OHad})$ term in the kinetic equation for the ORR]. Additional confirmation that the fractional coverage by the spectator species are indeed controlling the kinetics of the ORR was found by analyzing the results in the potential region where the adsorption of hydrogen takes place (E<0.2 V). Because of the lower coverage by $H_{upd}$, the production of peroxide is substantially attenuated on the Pt-skin surface. At the fuel cell relevant potentials (E>0.8 V), the observed catalytic activity for the ORR on $Pt_3Ni\{111\}$ is the highest that has ever been observed on cathode catalysts.

Figures 9A, 9B, 9C:
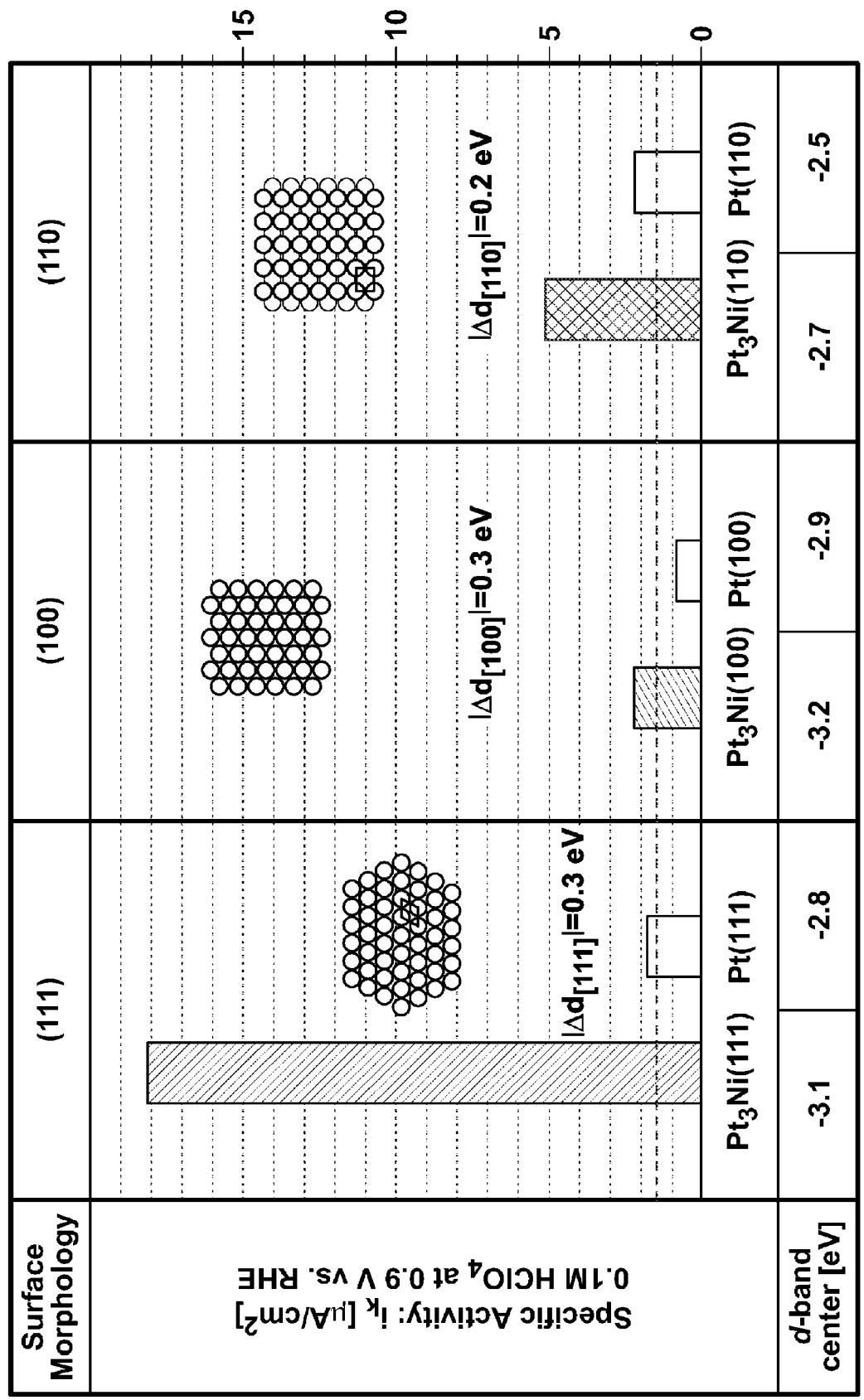
FIG. 9A shows the influence of crystallographic surface morphology and electronic surface properties on kinetics of ORR with RRDE measurements made for ORR in HClO$_4$ (0.1M) at 333k with 1600 revolutions per minute on a {111} surface for Pt$_3$Ni versus Pt{111}.
FIG. 9B show results for a {100} surface and FIG. 9C show results for a {110} surface.

FIGS. 9A-9C illustrate the synergy between surface geometry and surface electronic structure for the ORR. As summarized, the different low-index surfaces have markedly different activity for this reaction, that is, Pt$_3$Ni{100}-skin<Pt$_3$Ni{110}-skin<<<Pt$_3$Ni{111}-skin, with the change in activity between the least active {100} and the most active {111} surfaces being greater than an order of magnitude. Structure sensitivity of the ORR on the Pt low-index single-crystal surfaces in perchloric acid is established, with activities increasing in the order Pt{100}<<Pt{111}<Pt{110} (see FIGS. 9A-9C). These differences are attributable to the structure-sensitive adsorption of OH$_{ad}$ on Pt(hkl) and its inhibiting (site blocking) effect on O$_2$ adsorption. In the potential region of OH adsorption, the structure sensitivity of the Pt$_3$Ni(hkl)-skin surfaces has the same origin.

To reveal the role of the electronic structure in ORR kinetic, electrodes with the same surface morphology are compared. The most pronounced effect was observed on the {111} surfaces. For the same p(1×1) arrangement of the topmost layer, the same surface atomic density, and the same surface composition (100 percent Pt) but for a different electronic structure (|Δd$_{\{111\}}$|=0.34 eV, where |Δd$_{\{hkl\}}$| is the d-band center shift), the ORR is enhanced by a factor of 10 on Pt{111}-skin relative to that on Pt{111}. Given that extended Pt surfaces have 5 to 10 times the activity per surface Pt atoms than the state-of-the-art Pt/C catalysts that are currently used in the PEMFC (about 0.2 mA/cm$^2$ at 0.9V), a total of a 90-fold enhancement in Pt{111}-skin over Pt/C has been achieved.

In a preferred embodiment because the Pt$_3$Ni{111}-skin surface exhibits the highest catalytic activity that presently known, this alloy configuration and crystallographic orientation may be disposed on various substrates to obtain the desired enhancements in a fuel cell such as improved activity, stability and lower Pt content. This would reduce the current value of specific power density in a PEMFC of about 1.0 g of Pt per kW of Pt without loss in cell voltage, while maintaining the maximum power density (W/cm$^2$). Experiments demonstrate the ability to create and control the Pt-skin surface as well as nanosegregated near surface formations in a series of Pt-multi-metallic alloys with transition metals. Multi-metallic fuel cell catalysts may employ annealing as a key step in engineering of nanosegregated surfaces with superior catalytic properties.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of preparing a nanosegregated Pt alloy having enhanced catalytic properties, comprising:
    providing a sample comprising Pt$_3$Ni single crystal;
    providing a substantially inert and/or reductive environment; and
    annealing the sample in the substantially inert environment for a period and at a temperature profile to form a nanosegregated Pt alloy having a first layer consisting essentially of Pt, a second layer having an elevated level of Ni relative to the Pt$_3$Ni single crystal, and a third layer having an elevated level of Pt relative to the Pt$_3$Ni single crystal, wherein the alloy of Pt has a crystallographic orientation selected from the group of a {110} and a {111} orientation and the alloy layer of Pt having an electronic d band level downshifted relative to bulk Pt.

2. The method of claim 1, wherein the annealing period is from about 120 minutes to about 1000 minutes 3. The method of claim 1, wherein the temperature profile is a substantially constant temperature between about 350° C. to about 1000° C.

4. The method of claim 3, wherein the annealing period is from about 20 minutes to about 360 minutes.

5. The method of 1 wherein, the inert environment comprises an atmosphere of N$_2$, H$_2$, or Ar gas and mixtures thereof or vacuum conditions.

6. The method of claim 1, wherein the content of the second layer is from about 30 percent to about 70 percent Ni, and wherein the content of the third layer is from more than about 75 percent to about 95 percent Pt.

7. The method of claim 1, wherein the annealing period and temperature are selected such that the nanosegregated Pt alloy is characterized by suppressed underpotentially deposited hydrogen region from cyclic voltammetry.

8. The method of claim 1, wherein the period and temperature are selected such that the nanosegregated Pt alloy is characterized by a surface activity of at least about 2.0 mA/cm$^2$ at 0.9V.

9. The method of claim 1, further comprising: disposing the nanosegregated Pt alloy on at least one substrate for use in a fuel cell, wherein the substrate is selected from the group consisting of: carbon, metal oxides, metals, carbon nanotubes, and nanowires.

10. A nonsegregated Pt$_3$Ni alloy having enhanced catalytic properties, comprising:
    a layer of the Pt$_3$Ni layer having a crystallographic orientation selected from the group {111}, {110} and {100} orientation and further including one or more layers proximate to a surface of the alloy layer, the one or more layers including a first surface layer consisting essentially of pure Pt, a second layer having an elevated level of Ni of more than about 30% mole percent of the alloy of Pt, and a third layer having an elevated level of Pt but less than pure Pt, each of the one or more layers having a concentration of a surface layer consisting essentially of a bulk concentration of Pt in the alloy and remaining ones of the one or more layers having a lesser percentage of Pt, and wherein d band states of the alloy of Pt layer are downshifted relative to the bulk concentration of Pt.

11. The nanosegregated Pt alloy of claim 10, wherein the alloy comprises PtNi characterized by a substantially {111} crystallographic orientation.

12. The nanosegregated Pt alloy of claim 10, wherein the content of the second layer is from about 30 percent to about 60 percent Ni, and wherein the content of the third layer is from about 75 percent to about 95 percent Pt.

13. The nanosegregated Pt alloy of claim 10, wherein the first layer is characterized by suppressed underpotentially deposited hydrogen region from cyclic voltammetry.

14. The nanosegregated Pt alloy of claim 10, wherein the nanosegregated Pt alloy is in a form comprising at least one of a thin film or a nano-cluster.

15. The nanosegregated Pt alloy of claim 10, wherein the nanosegregated Pt alloy comprises nanoparticles disposed on a high surface area carbon substrate.

* * * * *